United States Patent [19]

Gazale

[11] Patent Number: 4,697,586
[45] Date of Patent: Oct. 6, 1987

[54] COMBINED CHISEL-GUIDE SURGICAL INSTRUMENT

[76] Inventor: William J. Gazale, 12423 Henderson Rd., Clifton, Va. 22024

[21] Appl. No.: 877,778

[22] Filed: Jun. 24, 1986

[51] Int. Cl.$^4$ .............................................. A61F 5/04
[52] U.S. Cl. ............................ 128/92 V; 128/92 VT
[58] Field of Search ............... 128/305, 304, 303 R, 128/92 R, 92 V, 92 VT, 751, 753, 754

[56] References Cited

U.S. PATENT DOCUMENTS

| | | | |
|---|---|---|---|
| D. 126,718 | 4/1941 | Grieshaber | D2/156 |
| D. 182,850 | 5/1958 | Reymann | D24/28 |
| D. 264,799 | 6/1982 | Osada | D8/99 |
| 2,235,419 | 3/1941 | Callahan et al. | 128/92 VD |
| 2,705,949 | 4/1955 | Silverman | 128/754 |
| 3,800,783 | 4/1974 | Jamshidi | 128/754 |
| 3,961,621 | 6/1976 | Northved | 128/753 |
| 4,150,675 | 4/1979 | Comparetto | 128/92 V |
| 4,153,053 | 5/1979 | Figallo | 128/92 VT |
| 4,243,048 | 1/1981 | Griffin | 128/751 |
| 4,314,565 | 2/1982 | Lee | 128/753 |
| 4,378,810 | 4/1983 | Ishizaki et al. | 128/754 |
| 4,423,721 | 1/1984 | Otte et al. | 128/92 VT |
| 4,433,681 | 2/1984 | Comparetto | 128/92 V |
| 4,438,769 | 3/1984 | Pratt et al. | 128/92 VT |
| 4,469,109 | 9/1984 | Mehl | 128/753 |
| 4,580,563 | 4/1986 | Gross | 128/92 VT |

FOREIGN PATENT DOCUMENTS

| | | | |
|---|---|---|---|
| 202970 | 10/1983 | German Democratic Rep. | 128/92 V |
| 858791 | 8/1981 | U.S.S.R. | 128/92 V |

Primary Examiner—C. Fred Rosenbaum
Assistant Examiner—C. W. Shedd
Attorney, Agent, or Firm—R. Martin Oliveras

[57] ABSTRACT

A combined chisel-guide surgical instrument for performing osteotomy and other procedures on the vertebra comprises: at least one chisel each including at least one front cutting edge for penetrating into the vertebra; a guide including a guide tip being locatable within the respective intervetebral space for accommodating and directing the motion of the chisel cutting edges into the vertebra; a handle being fixedly connected to the guide for directing and placing the guide tip into the intervertebral space; a front impact member being fixedly connected to the rear end of the chisel; a cylindrical member being fixedly connected to the front impact member; a rear impact member being fixedly connected to the cylindrical member; and an impact hammer being slidable along the cylindrical member and being impactable upon the front impact member to cause penetration of the chisel cutting edges into the vertebra and being impactable upon the rear impact member to cause extraction of the chisel cutting edges from the vertebra.

8 Claims, 18 Drawing Figures

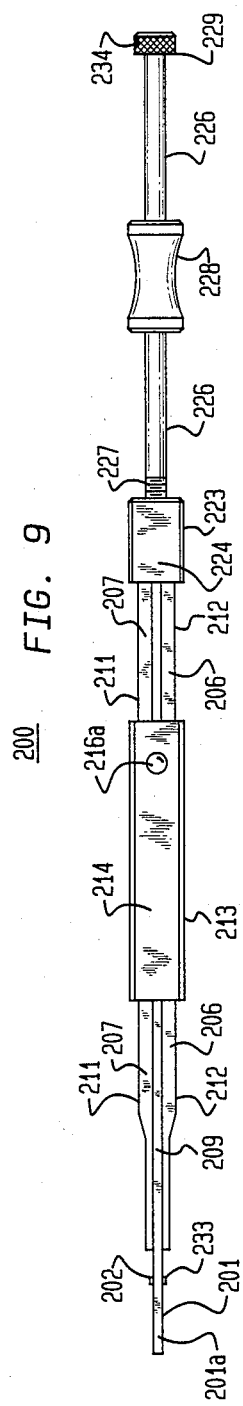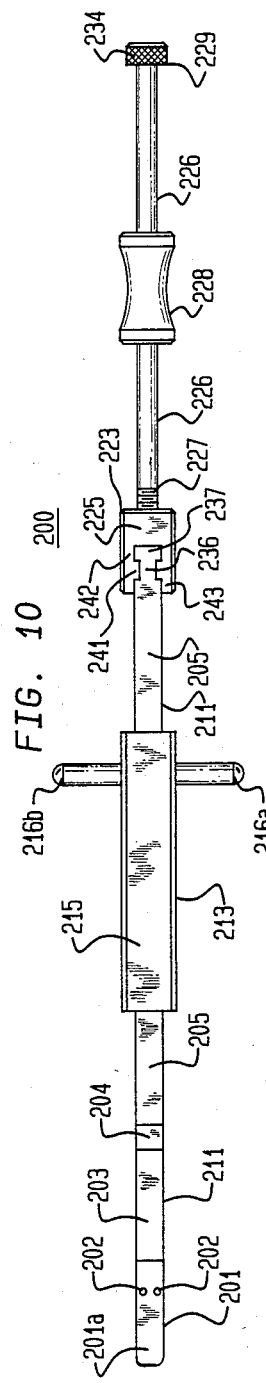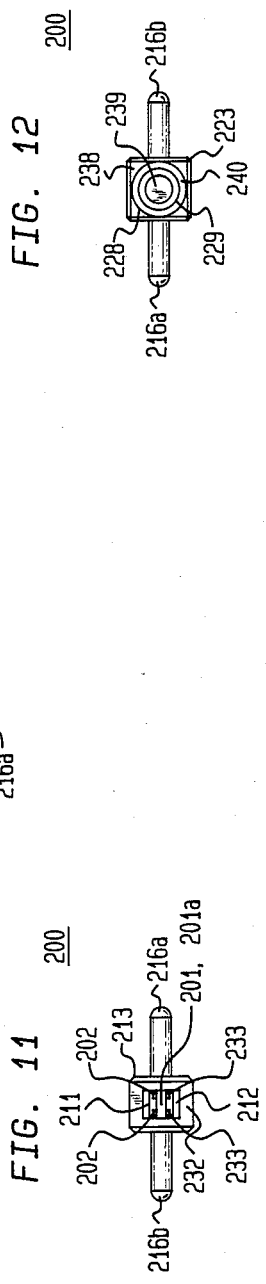

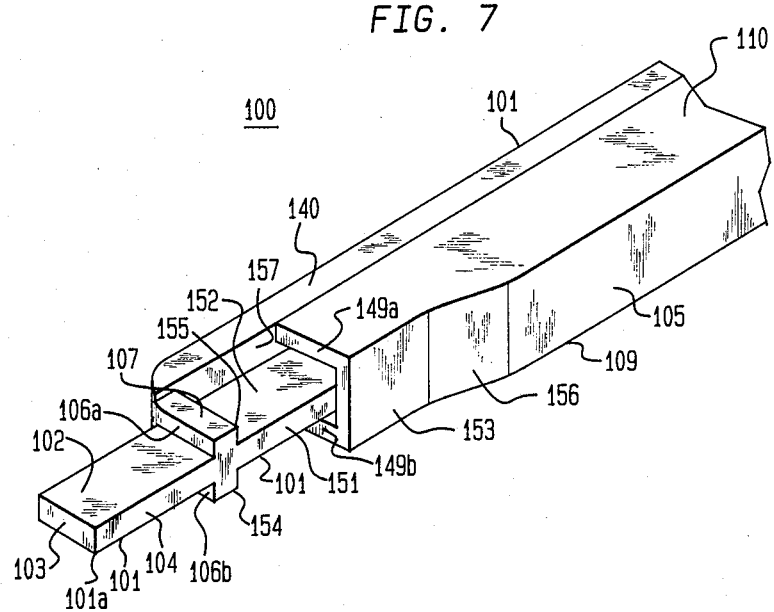
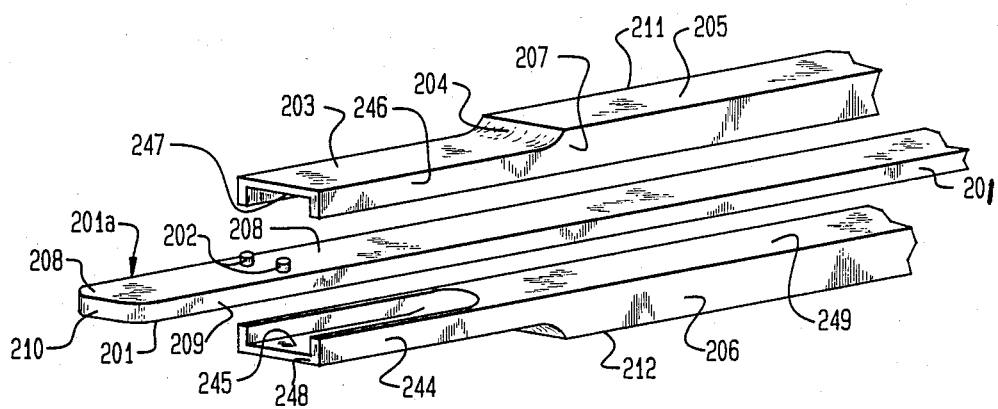

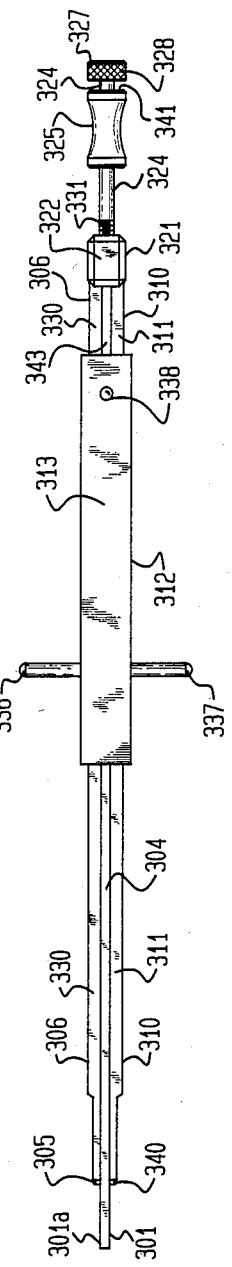
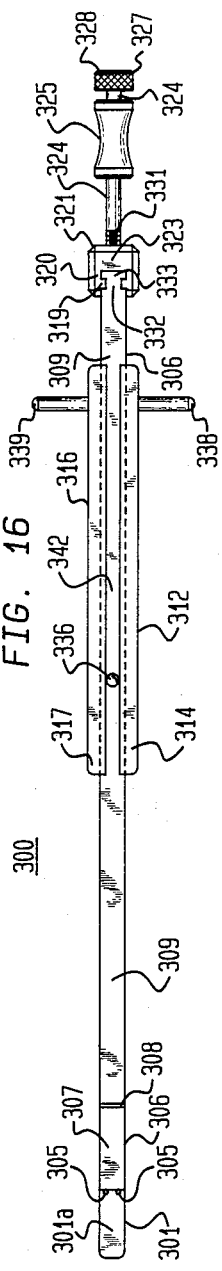
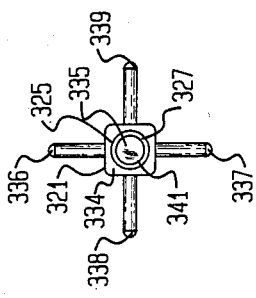
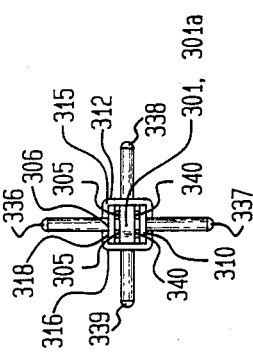

COMBINED CHISEL-GUIDE SURGICAL INSTRUMENT

FIELD OF THE INVENTION

This invention relates to surgical instruments and in particular to a combined chisel-guide instrument useful in performing osteotomy procedures and the like.

OTHER RELATED APPLICATIONS

This utility patent application is related to the following prior design patent applications by the same applicant herein: application Ser. No. 782,933 filed on Oct. 2, 1985 and being entitled "Combined Single Chisel-Guide Surgical Instrument Design"; application Ser. No. 782,935 filed on Oct. 2, 1985 and being entitled "Combined Double Chisel-Guide Surgical Instrument Design"; and application Ser. No. 782,934 filed on Oct. 2, 1985 and being entitled "Combined Double Chisel-Guide Surgical Instrument Design".

DISCUSSION OF THE PRIOR ART

Several prior art surgical devices and tools are disclosed as follows:

Silverman U.S. Pat. No. 2,705,949 entitled "Biopsy Needle" discloses a biopsy instrument having an outer tube and an inner split needle passing therethrough, the tube and needle being capable of independent advancement, means for limiting the permitted distance of advancement of the tube to the same distance of advancement permitted for the needle, and means for positioning the ends of the tube and the needle at the surface of the tissue prior to advancement of the tube and the needle. Specifically disclosed are inner needle 11, outer tube 12, base 14, hub 17, and flanges 21, 22, and 25;

Jamshidi U.S. Pat. No. 3,800,783 entitled "Muscle Biospy Device" discloses a biopsy means comprising blade means, hollow rectangular sheath means, a slot formed in the blade means, and a rigid bard. Specifically disclosed are hollow rectangular sheath means 20, tapered section 21, surfaces 12 and 13, slot 23, hook section 24, and point 25;

Northeved U.S. Pat. No. 3,961,621 entitled "Surgical Tool For Taking Biological Samples" discloses a surgical instrument comprising an elongate tubular needle, an elongate stiletto, means for guiding light from an external source, means for guiding a reflected image, and fine air ducts. Specifically disclosed are needle 1, stiletto 2, tube wall 3, core 5, and fibre bundles 7.

Griffin Pat. No. 4,243,048 entitled "Biopsy Device" discloses a surgical device comprising an elongated shaft, a rounded plastic member, a hollow metallic tubular blade member, and an annular cutting element. Specifically disclosed are anvil 13, cutting blade 30, shaft 10, tubular shaft 34, tubular member 40, handle 15, and knob 44;

Lee U.S. Pat. No. 4,314,565 entitled "Biopsy And Aspiration Needle Unit" discloses a biopsy needle unit comprising a holding means, a replaceable cannula, interlocking means, an elongated stylet, and engaging means. Specifically disclosed are replaceable cannula 24, collar nut 15, holding means 10, and stylet 33;

Ishizaki U.S. Pat. No. 4,378,810 entitled "Assembly For Performing Biopsies Using A Combination Probe-Guide" discloses an assembly comprising a hollow tubular member, handle means, and a needle within the tubular member. Specifically disclosed are syringe 44, hub 42, spacer 48, probe guide 12, and needle 40; and Mehl U.S. Pat. No. 4,469,109 entitled "Bone Marrow Aspiration Needle" discloses a needle comprising a cannula member, a stylet member, and a threaded depth stop means. Specifically disclosed are cannula 17, skirt 74, threaded portion 70, and molded housing 20.

Other devices and tools are disclosed in the following design patents as follows: Grieshaber U.S. Pat. No. 126,178 entitled "Adenotome"; Reymann U.S. Pat. No. 182,850 entitled "Surgical Chisel Or The Like"; and Osada U.S. Pat. No. 264,799 entitled "Cutter Knife".

The cited prior art patents do not appear to disclose the combined chisel-guide structure of applicant nor the operation of the combined structure elements of applicant with respect to instruments useful in performing osteotomies or the like.

Objects of the present invention are therefor to provide:

a surgical instrument that is useful in operations of the vertebra;

a surgical instrument that is useful in performing osteotomy procedures or the like on the human vertebra and other bony structures of the body;

a surgical instrument that is useful in a posterior lumber intervertebral fusion operation; and a surgical instrument that is useful in the procedure called epiphysiodesis.

SUMMARY OF THE PRESENT INVENTION

A combined chisel-guide surgical instrument for performing osteotomy and other procedures on the human vertebra comprises: at least one longitudinally directed and movable chisel each including at least one front cutting edge for penetrating into the vertebra; a longitudinally directed guide including a front guide tip being locatable within the intervertebral space for accommodating and directing the motion of the chisel cutting edges into the vertebra; a handle being fixedly connected to the rear extension of the guide for directing and placing the guide tip into the intervertebral space; a front impact block member being connected to the rear extension of the chisel; an intermediate longitudinally directed cylindrical member being fixedly connected to the rear end of the front impact block member; a rear impact cylindrical member being fixedly connected to the rear end of the intermediate cylindrical member; and a longitudinally movable impact hammer including a central hole and being accommodated by the intermediate cylindrical member; wherein the handle is utilized to cause forward penetration of the guide tip into the intervertebral space and to secure and fix the guide tip in such position; wherein the impact hammer is manually caused to strike the rear surface of the front impact block member to cause forward penetration of the chisel front cutting edge to the desired penetration depth in the vertebra; wherein the impact hammer is manually caused to strike the front surface of the rear impact cylindrical member to cause rearward retraction of the chisel front cutting edges from the vertebra; and wherein the handle is utilized to cause rearward retraction of the guide tip from the intervertebral space.

Features of the present invention are therefore that:

the guide tips that are utilized in the instrument may be of different thicknesses to accommodate intervertebral spaces of different widths in order to guarantee a tight fit of the guide tip within the intervertebral space;

the guide tip also serves as an intervertebral space depth gauge in addition to insuring the proper angle of chisel cut;

the guide tip is prevented from penetrating into the intervertebral space deeper than the anterior longitudinal ligament by surface extensions being located at the rearmost portion of the guide tip;

the chisel slides along and is guided longitudinally by a track surface being located on the guide;

the chisel is maintained in constant apposition with the guide by means of the handle;

in the two chisel embodiments, the impact hammer in combination with the front impact block member may be utilized to penetrate one vertebra with one chisel at a time or two vertebra with two chisels simultaneously;

in the two chisel embodiments, the impact hammer in combination with the front impact block member and the rear impact cylindrical member may be utilized to extract one chisel at a time from the vertebra or two chisels simultaneously;

in the one chisel embodiment, the chisel includes two front cutting edges wherein each front cutting edge penetrates a respective vertebra;

in the two chisel embodiments, each chisel includes one front cutting edge wherein each chisel front cutting edge penetrates a respective vertebra;

in the two chisel embodiments, the front impact block member also serves as a disengageable coupler for the chisels such that the front impact block member may be vertically slid off the rear ends of the chisels to thereafter allow retraction of either chisel or to thereafter allow penetration of either chisel independently of the other chisel;

in the second two chisel embodiment, the handle member may be retracted together with the guide and guide tip to thereafter allow manipulation of either or both chisels which remain penetrated into the vertebra and thus to allow removal of the osteotomized portions of the vertebra with the chisels.

Advantages of the present invention are therefore that:

one is able to know and control the depth of penetration of the guide tip into the intervertebral space;

there is minimal rotation of the instrument once the guide tip has penetrated into the intervertebral space;

there is a reduction in the time of the respective osteotomy procedures especially with repsect to the second two chisel embodiment such that complications and blood loss are also reduced; and that several guide tip thicknesses may be utilized with the same instrument chisel configuration to accommodate different intervertebral space widths.

Description Of The Drawing

The above and other objects, features, and advantages of the present invention will be better appreciated from a reading of the following detailed description with reference to the drawing in which:

FIG. 7 is a perspective view showing in detail the front end thereof;

FIG. 9 is a lateral view thereof;
FIG. 10 is a top view thereof;
FIG. 11 is a front view thereof;
FIG. 12 is a rear view thereof;
FIG. 13 is an exploded perspective view showing in detail the front end thereof;
FIG. 15 is a lateral view thereof;
FIG. 16 is a top view thereof;
FIG. 17 is a front view thereof;
and
FIG. 18 is a rear view thereof.

DETAILED DESCRIPTION

Figure 1:
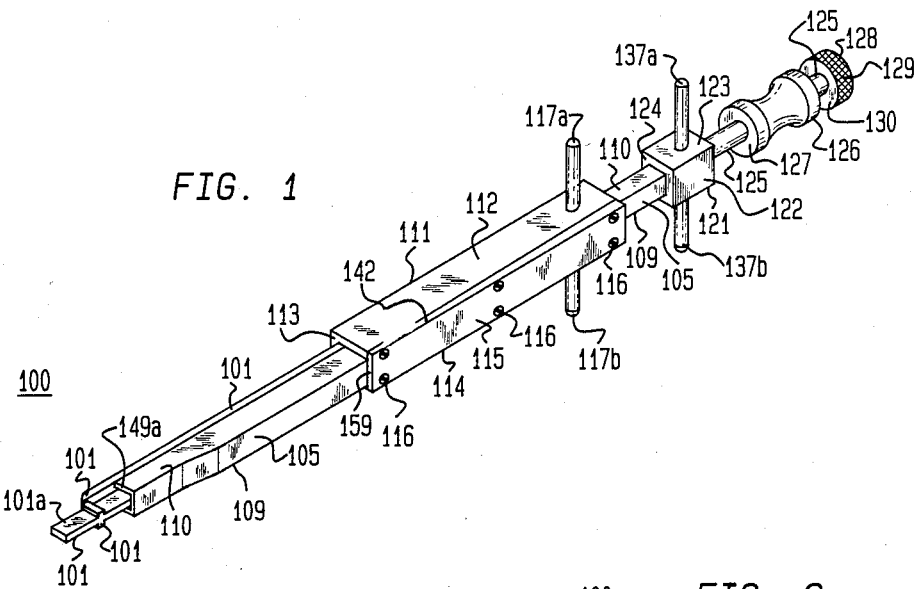
FIG. 1 is a perspective view of the one chisel embodiment of a surgical instrument according to the present invention.

FIG. 1 is a perspective view of the one chisel embodiment of a surgical instrument according to the present invention. Surgical instrument 100 comprises: front guide 101 including front guide tip 101a; front U-shaped chisel 109 including lateral surface 105, front cutting edge 149a, and upper surface 110; handle 111 being fixedly attached to the rear end of guide 101 and including upper surface 112, front surface 113, front vertical cylindrical cross rods 117a and 117b, lateral plate 114 being fixedly attached to member 111 via screws 116 at lateral surface 115 of plate 114; front impact block member 121 being fixedly attached to the rear end of chisel 109 and including lateral surface 122, upper surface 123, front surface 124, and rear vertical cylindrical cross rods 137a and 137b; intermediate longitudinally directed cylindrical member 125 being fixedly attached to the rear end of member 121; impact hammer 126 being longitudinally slidable on member 125 and including front surface 127; and rear impact cylindrical member 128 being fixedly attached to the rear end of member 125 and including knurled surface 129 and front surface 130. Plate 115 also includes upper surface 142 and front surface 159.

Figure 2:
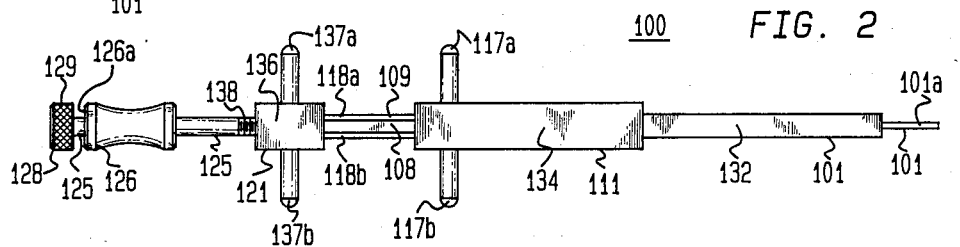
FIG. 2 is a first lateral view thereof.

FIG. 2 is a first lateral view of surgical instrument 100 showing: guide 101 including guide tip 101a and lateral surface 132; chisel 109 including upper and lower lateral extensions 118a and 118b, and lateral surface 108 being on the opposite side of surface 105; handle 111 including lateral surface 134 being opposite surface 115 of plate 114, and rods 117a and 117b; member 121 including lateral surface 136 being opposite surface 122, and rods 137a and 137b being fixedly attached to member 121; member 125 including threaded portion 138 being screwed onto a threaded hole being located on the rear surface of member 121; impact hammer 126; and member 128 including surface 129. Hammer 126 also includes rear surface 126a.

Figure 3:
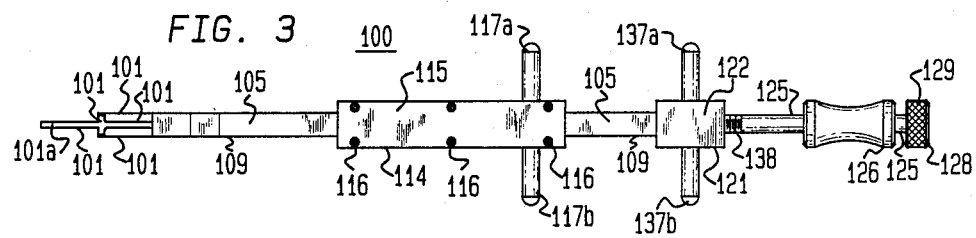
FIG. 3 is a second lateral view thereof.

FIG. 3 is a second lateral view of surgical instrument 100 showing: guide 101 including guide tip 101a; chisel 109 including surface 105; plate 114 including surface 115, screws 116, and rods 117a and 117b of handle 111; member 121 including surface 122 and rods 137a and 137b; member 125 including threaded portion 138; impact hammer 126; and member 128 including surface 129.

Figure 4:
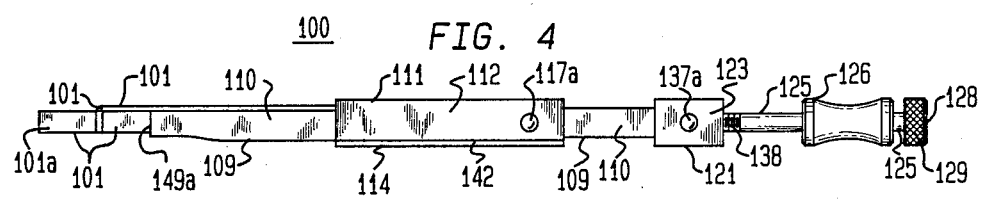
FIG. 4 is a top view thereof.

FIG. 4 is a top view of surgical instrument 100 showing: guide 101 including guide tip 101a; chisel 109 including surface 110 and upper front cutting edge 149a; handle 111 including surface 112, plate 114, and rod 117a; member 121 including surface 123 and rod 137a;

member 125 including threaded portion 138; impact hammer 126; and member 128 including surface 129.

Figure 5:
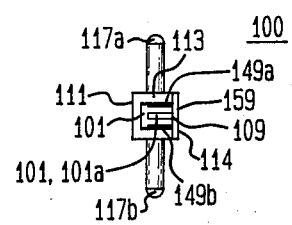
FIG. 5 is a front view thereof.

FIG. 5 is a front view of surgical instrument 100 showing: guide 101 including guide tip 101a; chisel 109 including upper and lower front cutting edges 149a and 149b; and handle 111 including plate 114 having surface 159, surface 113, and rods 117a and 117b.

Figure 6:
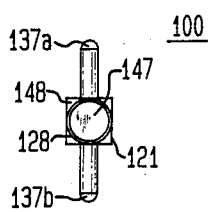
FIG. 6 is a rear view thereof.

FIG. 6 is a rear view of surgical instrument 100 showing: member 121 including surface 148 and rods 137a and 137b; and member 128 including rear surface 147.

FIG. 7 is a perspective view showing in detail the front end of surgical instrument 100 showing: guide 101 including front vertical surface 103, front upper surface 102, front lateral surface 104, upper vertical surface 106a and lower vertical surface 106b, intermediate upper surface 107, rear upper surface 152, rear lateral surface 151, lateral vertical surface 157, rear upper surface 140, upper projection 155, and lower projection 154; chisel 109 including upper surface 110, front lateral surface 153, rearward lateral surface 105, upper and lower front cutting edges 149a and 149b, and intermediate lateral surface 156. Guide tip 101a is defined by surfaces 102, 103, 104, and back to surfaces 106a and 106b of projections 155 and 154. Guide tip 101a also serves as a depth gauge during penetration of guide 101 into the intervertebral space. Front upper and lower chisel cutting edges 149a, b are the anteriormost edges of surface 110 and the lower surface of chisel 109 being opposite to surface 110. Chisel 109 is accommodated by and slides along surface 157 and surface 107 of guide 101. Forward motion of hammer 126 causes surface 127 thereof to strike surface 148 of member 121 thereby transferring such impact forward longitudinally along member 121 and chisel 109 to further cause penetration of front chisel cutting edges 149a and 149b into the respective vertebra associated with the intervertebral space into which guide tip 101a has been inserted back to projections 155 and 154. Rearward motion of hammer 126 causes surface 126a to strike surface 130 of member 128 thereby transferring such impact rearwardly longitudinally along member 128, member 125, member 121, and chisel 109. Chisel 109 may be stabilized during the operation by manually holding onto rods 137a and 137b of member 121. Instrument 100 may be stabilized in general during the operation by manually holding onto rods 117a and 117b of handle 111.

The operation of surgical instrument 100 is a follows: in step 1, tip 101a of guide 101 is inserted up to projections 155 and 154 into the dorsal aspect of the respective intervertebral space; in step 2, chisel 109 is slid onto handle 111 and along surface 157 of guide 101 until front upper and lower cutting edges 149a and 149b of chisel 109 envelope surface 107 of upper projection 155 and the similar surface of lower projection 154 such that upper and lower cutting edges 149a and 149b of chisel 109 rest onto the dorsal aspect of the respective upper and lower vertebra; in step 3, using impact hammer 126 as explained above, forward penetration of chisel front cutting edges 149a and 149b is effected into the respective vertebral plates somewhat above and below the subject intervertebral space but not all the way forward to the ventral aspect of such vertebra; in step 4, chisel 109 is extracted from such vertebra by applying rearward motion to hammer 126 as explained above thereby leaving guide tip 101a inserted into the intervertebral space; in step 5, guide 101 is then extracted from the intervertebral space by the application of rearward force to handle 111 and rods 117a and 117b thereby leaving behind the already osteotomized vertebral plates. Thereafter, the already osteotomized vertebral plates are removed using known techniques.

Figure 8:
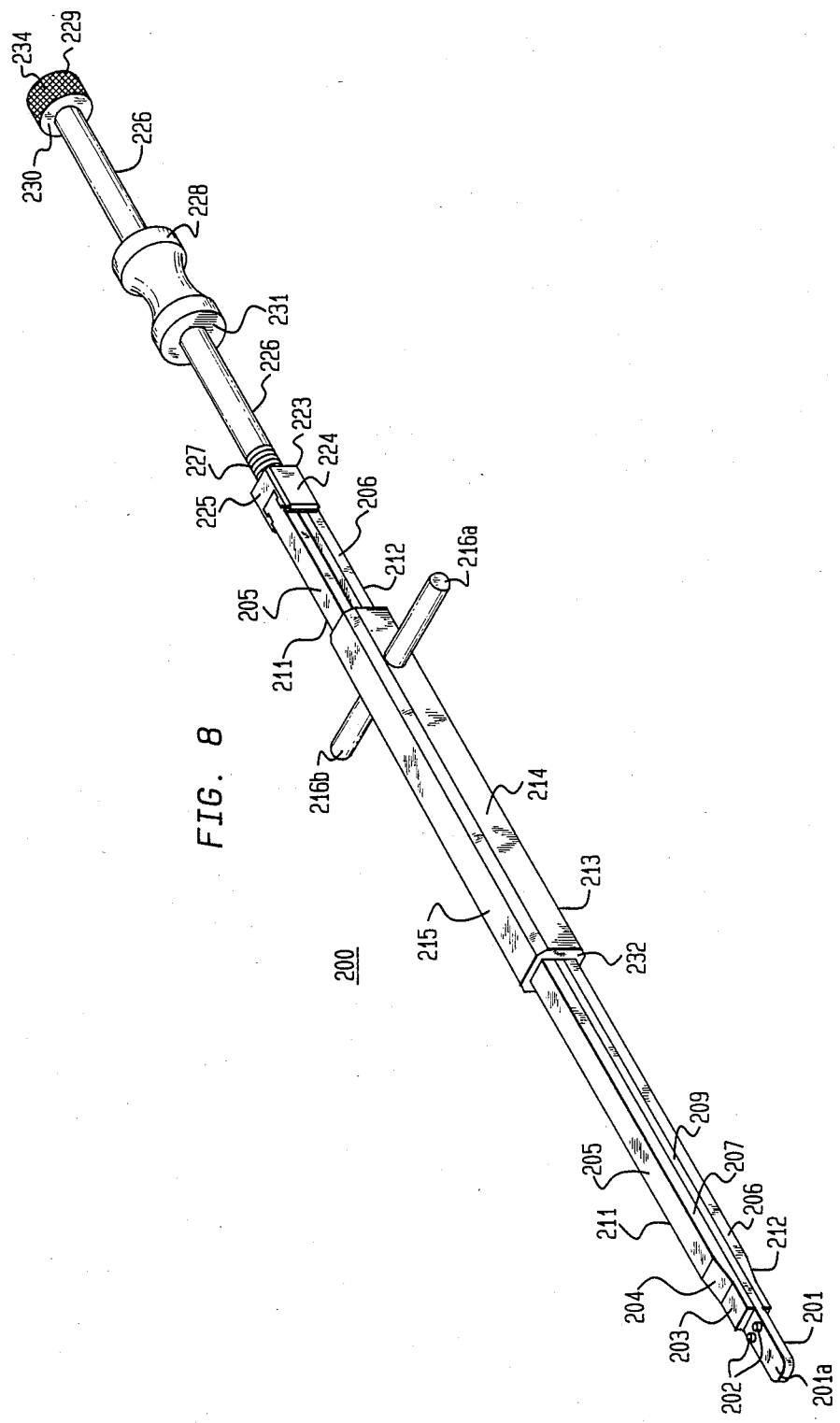
FIG. 8 is a perspective view of the first two chisel embodiment of a surgical instrument according to the present invention.

FIG. 8 is a perspective view of the first two chisel embodiment of a surgical instrument according to the present invention. Instrument 200 comprises: front guide 201 including guide tip 201a, lateral surface 209, and upper projections 202; upper U-shaped chisel 211 including upper surface 203, slanted surface 204, upper surface 205, and lateral surface 207; lower U-shaped chisel 212 including lateral surface 206; handle 213 including lateral surface 214, upper surface 215, front surface 232, and horizontal cylindrical rods 216a and 216b; combination front impact block member-chisel coupler 223 including lateral surface 224 and upper surafce 225; intermediate cylindrical member 226 including threaded portion 227; impact hammer 228 including front surface 231; and rear impact cylindrical member 229 including knurled surface 234 and front surface 230. Handle 213 is connected to the rear end of guide 101; member 223 is slidably coupled to the rear ends of chisels 211 and 212; member 226 is disengageably threaded onto the rear end of member 223; and member 229 may be a fixed portion of the rear end of member 226. Hammer 228 slides longitudinally along member 226.

FIG. 9 is a lateral view of surgical instrument 200 showing: guide 201 including guide tip 201a, lateral surface 209, and upper and lower projections 202 and 233; chisel 211 including surface 207; chisel 212 including surface 206; handle 213 including surface 214 and rod 216a; member 223 including surface 224; member 226 including threaded portion 227; impact hammer 228; and member 229 including surface 234.

FIG. 10 is a top view of surgical instrument 200 showing: guide 201 including guide tip 201a and projections 202; chisel 211 including surface 205 having narrowed portion 236 and rear portion 237, surface 203, and surface 204; handle 213 including surface 215 and rods 216a and 216b; member 226 including threaded portion 227; impact hammer 228; member 229 including surface 234; and member 223 including surface 225 having front narrowed portion 243, intermediate expanded portion 241, and rear narrowed portion 242.

FIG. 11 is a front view of surgical instrument 200 showing: guide 201 including guide tip 201a and projections 202 and 233; chisel 211; chisel 212; and handle 213 including surface 232 and rods 216a and 216b.

FIG. 12 is a rear view of surgical instrument 200 showing: member 229 including rear surface 239; impact hammer 228 including rear surface 240; member 223 including rear surface 228; and rods 216a and 216b of handle 213.

FIG. 13 is an exploded perspective view showing in detail the front end of surgical instrument 200 showing: guide 201 including front curved surface 210, upper surface 208, lateral surface 209, and upper projections 202; chisel 211 including upper surface 205, intermediate surface 204, upper surface 203, narrowed lateral surface 246 being the front end of surface 207, and front cutting edge 247; and chisel 212 including lateral surface 206, upper surface 249, narrowed lateral surface 244 being the front end of surface 206, depressed upper surface 245, and front cutting edge 248. Also shown is guide tip portion 201a back to projections 202 and 233.

The mode of operation of instrument 200 is similar to that of instrument 100 in that chisels 211 and 212 slide along common guide 201 in a forward direction to penetrate the respective vertebra after guide tip 201a back to projections 202 and 233 has been inserted into the respective intervertebral space. Front chisel cutting edges 247 and 248 penetrate into the vertebra by causing hammer 228 to strike member 223 as explained above. In instrument 100, chisel 109 includes two front cutting edges each being parallel to the upper and lower surfaces of guide 101 whereas in instrument 200 each chisel 211 and 212 includes one cutting edge each being parallel to the upper and lower surfaces of guide 201. In instrument 200, chisels 211 and 212 may be decoupled from each other by sliding member 223 vertically away from the chisels in which case either chisel mey be struck forwardly or rearwardly independently of the other by way of member 223 or by just tapping the rearmost end of the chisel accordingly. Handle 213 and rods 216a and 216b are utilized to stabilize overall instrument 200 during the operation within the respective intervertebral space. Once the vertebra have been osteotomized by the respective chisels, then chisels 211 and 212 may be retracted or removed from the osteotomized vertebra together using member 223 or individually after having slidably disengaged member 223 from the chisels. Thereafter, guide 201a is retracted from the intervertebral space using handle 213 and rods 216a and 216b. Finally, the osteotomized vertebral portions or plates are removed using known techniques.

Figure 14:
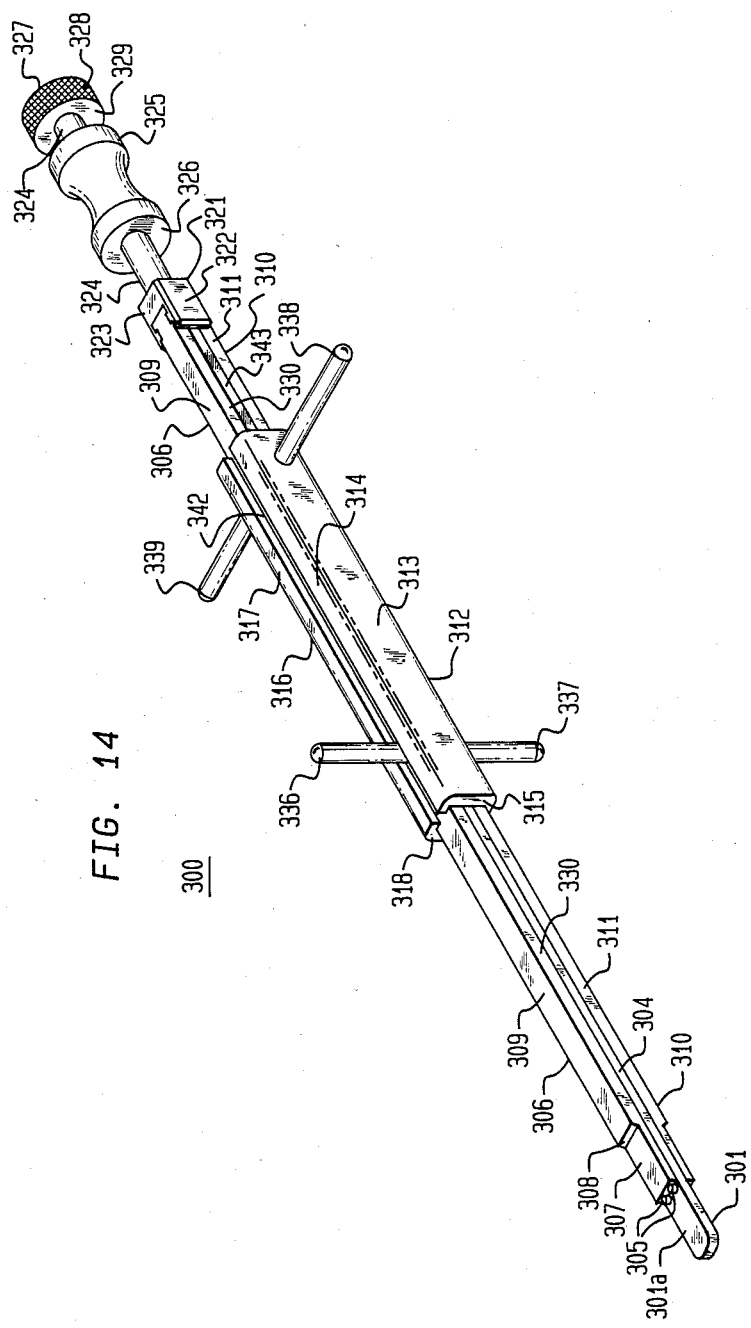
FIG. 14 is a perspective view of the second two chisel embodiment of a surgical instrument according to the present invention.

FIG. 14 is a perspective view of the second two chisel embodiment of a surgical instrument according to the present invention. Instrument 300 comprises: guide 301 including guide tip 301a and upper projections 305; upper U-shaped chisel 306 including upper surface 307, slanted surface 308, upper surface 309, upper vertical cylindrical rod 336, and lateral surface 330; lower U-shaped chisel 310 including lateral surface 311 and lower vertical cylindrical rod 337; lateral handle member 312 including lateral surface 313, upper surface 314, front surface 315, and lateral horizontal cylindrical rod 338; lateral handle member 316 including upper surface 317, front surface 318, and lateral horizontal cylindrical rod 339; combination front impact block member-chisel coupler 321 including upper surface 323 and lateral surface 322; intermediate cylindrical member 324; impact hammer 325 including front surface 326; and rear impact cylindrical member 327 including knurled surface 328 and front surface 329. Members 316 and 312 are connected to the rear end of guide 301; member 321 is disengageably coupled to the rear ends of chisels 306 and 310; member 324 is screwed onto the rear surface of member 321; member 327 may be fixed portion of the rear end of member 324; and hammer 325 slidably moves longitudinally along member 324. Guide 301 also includes lateral surface 304 while members 312 and 316 define slot 342.

FIG. 15 is a lateral view of surgical instrument 300 showing: guide 301 including guide tip 301a and upper and lower projections 305 and 340; chisel 306 including surface 330 and rod 336; chisel 310 including surface 311 and rod 337; member 312 including surface 313 and rod 338; member 321 including surface 322; member 324 including threaded portion 331; impact hammer 325 including rear surface 341; and member 327 including surface 328. Guide 301 also includes surface 304. Space 343 is located in between chisels 306 and 310 at the rear.

FIG. 16 is a top view of surgical instrument 300 showing: guide 301 including guide tip 301a and projections 305; chisel 306 including surface 307, surface 308, rod 336, and surface 309 having narrowed portion 332 and rear portion 333; member 312 including surface 314 and rod 338; member 316 including surface 317 and rod 339; member 321 including surface 323 having expanded portion 319 and narrowed portion 320; member 324 including threaded portion 331; impact hammer 325; and member 327 including surface 328.

FIG. 17 is a front view of surgical instrument 300 showing: guide 301 including guide tip 301a and projections 305 and 340; chisel 306 including rod 336; chisel 310 including rod 337; member 312 including surface 315 and rod 338; and member 316 including surface 318 and rod 339.

FIG. 18 is a rear view of surgical instrument 300 showing: member 327 including rear surface 335; member 321 including rear surface 334; rod 336 of chisel 306; rod 337 of chisel 310; rod 338 of member 312; and rod 339 of member 316. Also shown is rear surface 341 of hammer 325.

The front end of surgical instrument 300 is similar to that of surgical instrument 200 shown in FIG. 13.

With respect to surgical instrument 300: the overall handle structure includes members 312 and 316 which are held together by a unitary rod comprising rods 338 and 339; such overall handle structure may be removed from instrument 300 along with guide 301 from the respective intervertebral space while chisels 306 and 310 remain penetrated into the respective vertebra because longitudinal slot 342 is provided to allow relative sliding between rod 336 and members 312 and 316. A similar explanation applies to the underside of handles 312 and 316 and rod 337. Rods 336 and 337 allow for securing and stabilizing of chisels 306 and 310 in place penetrated into the respective vertebra even after the overall handle structure has been retracted and removed.

The mode of operation of surgical instrument 300 is as follows: insert guide tip 301a into the respective intervertebral space by pushing forward onto rods 338 and 339 of handle members 312 and 316; thereafter slide upper and lower chisels 306 and 310 together or one at a time along and onto the overall handle structure from the rear such that the front cutting edges of chisels 306 and 310 are on the proper dorsal aspect of the respective vertebra; thereafter drive chisels 306 and 310 together or individually forward into the respective vertebra by striking impact hammer 325 onto the rear surface of member 321 while holding the overall handle structure firmly using rods 338 and 339 until the front cutting edges of chisels 306 and 310 reach the proper depth; thereafter slide off member 321 from the rear ends of the chisels to also remove member 324, impact hammer 325, and member 327 as a unit; this will now allow the overall handle structure and guide 301 to slide out backwards as a unit while chisels 306 and 310 remain penetrated into the respective vertebra; this is done by carefully tapping backwards onto rods 338 and 339 until guide tip 301a has cleared the respective intervertebral space; thereafter rotate the front ends of chisels 306 and 310 individually or simultaneously until the osteotomized portions of the respective vertebra are loosened and extractable upon removal of chisels 306 and 310. A main feature of instrument 300 is that slot 342 allows for the removal of the overall handle structure before removal of chisels 306 and 310. With respect to surgical instruments 100 and 200, the respective chisels had to be retracted from the respective vertebra before the handle structures and the guides could be removed from the respective intervetebral spaces. Thereafter, with respect to instruments 100 and 200, the osteotomized vertebra had to be removed using known techniques but with separate and different instruments. With respect to instrument 300, the osteotomized vertebra may be removed using chisels 306 and 310 which are an inherent part of surgical instrument 300. This latter procedure using instrument 300 allows for shorter operating times and therefore results in a reduction of complications and a reduction in blood loss.

While the arrangement according to the present invention has been described in terms of specific illustrative embodiments, it will be apparent to those skilled in the art that many modifications are possible within the spirit and scope of the disclosed principle.

What is claimed is:

1. A surgical instrument for penetrating into at least one bony structure being adjacent to a space which is adjacent to such bony structure, said surgical instrument comprising:
   a longitudinally directed guide member including a front end, a rear end, a front lower surface, a front upper surface, and a front guide tip portion having at least one depth limiting projection being located on either of said front upper or front lower surfaces;
   a longitudinally directed handle member including a rear end, a first surface, a second surface, and at least one rod member being fixedly connected to either of said handle member first or second surfaces, said handle members being fixedly connected to said guide member;
   at least one longitudinally directed chisel member each including a rear end and at least one front cutting edge, said chisel member being longitudinally slidable within said handle member from the rear end to the front end of said handle member, and said chisel member being longitudinally slidable along said guide member front lower surface and front upper surface forward to said guide tip portion such that said chisel member rear end protrudes from said handle member rear end;
   a front impact member including a front end, a first surface, a second surface, and a rear surface, said front impact member front end being fixedly connected to said chisel member rear end;
   an intermediate longitudinally directed member including a front end, said intermediate member front end being connected to said front impact member rear end; and
   an impact hammer member including a front surface and a longitudinally directed central hole, said impact hammer member being accomodated by said intermediate member along said central hole and being longitudinally slidable along said intermediate member;
   wherein application of forward force to said handle member including said rod member causes forward penetration of said guide member tip portion into such space up to said limiting projection; and
   wherein application of forward motion to said impact hammer member causes said impact hammer member front surface to impact upon said front impact member rear surface thereby causing forward penetration of said chisel member front cutting edge into such bony structure.

2. The surgical instrument of claim 1 wherein said surgical instrument comprises one U-shaped chisel member including two front cutting edges each being parallel to said guide member upper and lower surface.

3. The surgical instrument of claim 1:
   wherein said impact hammer member further includes a rear surface;
   wherein said intermeidate member further includes a rear end; and
   wherein said surgical instrument further comprises a rear impact member including a front surface and being fixedly connected to said intermediate member rear end;
   wherein application of rearward motion to said impact hammer member causes said impact hammer rear surface to impact upon said rear impact member front surface thereby causing rearward retraction of said chisel member front cutting edge from such bony structure.

4. The surgical instrument of claim 1 wherein application of rearward force to said front impact member causes rearward retraction of said chisel member front cutting edge from such bony structure.

5. The surgical instrument of claim 1 wherein application of rearward force to said handle member including said rod member causes rearward retraction of said guide member front tip portion from such space.

6. The surgical instrument of claim 1 wherein said surgical instrument comprises longitudinally directed upper and lower chisel members each including one front cutting edge each being parallel to said guide member upper and lower surfaces.

7. The surgical instrument of claim 6 wherein said upper and lower chisel member rear ends are shaped and wherein said front impact member front end is also shaped such that said front impact member front end is accommodated by said chisel member rear ends and wherein said front impact member is slidable laterally onto and off said chisel member rear ends such that said front impact member, said intermediate member, said rear impact member, and said impact hammer may be removed as a unit away from said chisel member rear ends.

8. The surgical instrument of claim 7:
   wherein said handle member further includes first and second longitudinally directed lateral members;
   wherein said handle member rod member is common to and holds together said first and second lateral members such that there remains a longitudinal space or slot in between said first and second lateral members above and below said guide member upper and lower surfaces;
   wherein said upper and lower chisel members each further includes a rod member being located along and within said longitudinal space or slot; and
   wherein once said front impact member is removed from said chisel member rear ends, upon application of rearward force to said lateral handle members including said rod members, said handle members and said guide member may be rearwardly retracted such that said guide member front tip portion may be rearwardly extracted from such space and such that said chisel member front cutting edge may remain penetrated into such bony structure.

* * * * *